(12) United States Patent
Toth et al.

(10) Patent No.: US 6,266,434 B1
(45) Date of Patent: Jul. 24, 2001

(54) METHODS AND APPARATUS FOR REDUCING SPECTRAL ARTIFACTS IN A COMPUTED TOMOGRAPH SYSTEM

(75) Inventors: Thomas L. Toth, Brookfield; O. Erdogan Gurmen, Shorewood; Bing Shen, Milwaukee, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/118,397

(22) Filed: Jul. 17, 1998

(51) Int. Cl.[7] ..................................................... A61B 6/00
(52) U.S. Cl. ............................................ 382/131; 382/128
(58) Field of Search ........................... 382/50, 131, 128; 378/4, 62, 19; 128/653; 250/363, 385, 455; 600/436

(56) References Cited

U.S. PATENT DOCUMENTS

| | | | |
|---|---|---|---|
| 4,392,057 | * | 7/1983 | Mathieson et al. ............... 250/385 |
| 5,093,850 | * | 3/1992 | Dinwiddie et al. ............... 378/15 |
| 5,168,532 | * | 12/1992 | Seppi et al. ..................... 382/50 |
| 5,335,255 | * | 8/1994 | Seppi et al. ..................... 378/4 |
| 5,684,855 | * | 11/1997 | Aradate et al. .................. 378/4 |
| 5,692,507 | * | 12/1997 | Seppi et al. ..................... 128/653 |
| 5,812,629 | * | 9/1998 | Clauser .......................... 378/62 |
| 5,903,008 | * | 5/1999 | Li ................................ 250/363 |
| 5,961,457 | * | 10/1999 | Raylman et al. ................. 600/436 |
| 5,970,113 | * | 10/1999 | Crawford et al. ................ 378/19 |
| 6,115,448 | | 9/2000 | Hoffman ......................... 378/9 |

* cited by examiner

Primary Examiner—Leo Boudreau
Assistant Examiner—M. B. Choobin
(74) Attorney, Agent, or Firm—Armstrong Teasdale LLP; Christian G. Cabou

(57) ABSTRACT

Methods and apparatus for reducing spectral artifacts in a computed tomography (CT) system are described. In one embodiment, the CT system includes a plurality of multi-slice detector modules, a detector housing and a collimator adjacent the detector modules. Each detector module is mounted to the detector housing and includes a scintillator array. The collimator includes a plurality of plates that are positioned so that a x-ray beam shadow is centered over gaps in the scintillator array. In operation, the collimator separates the x-ray beams so that the scintillator gaps are protected and the x-ray beams are prevented from projecting through the scintillator array elements along a shortened length path.

17 Claims, 4 Drawing Sheets

METHODS AND APPARATUS FOR REDUCING SPECTRAL ARTIFACTS IN A COMPUTED TOMOGRAPH SYSTEM

FIELD OF THE INVENTION

This invention relates generally to computed tomograph (CT) imaging and, more particularly, to reducing spectral artifacts in a multislice CT system.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector. A scintillator is located adjacent the collimator, and photodiodes are positioned adjacent the scintillator.

Multislice CT systems are used to obtain data for an increased number of slices during a scan. Known multislice systems typically include detectors generally known as 2-D detectors. With such 2-D detectors, a plurality of detector elements form separate channels arranged in columns and rows. Each row of detectors forms a separate slice. For example, a two-slice detector has two rows of detector elements, and a four-slice detector has four rows of detector elements. During a multislice scan, multiple rows of detector cells are simultaneously impinged by the x-ray beam, and therefore data for several slices is obtained.

Multislice detectors are typically segmented into a series of individual scintillator cells in the X and Z axes. These scintillator cells can be separated by narrow gaps of only a few micrometers between adjacent cells. The gaps are filled with a light reflecting material. The detector elements could accept off-axis, or scattered, x-ray beams which decrease contrast resolution and increase image artifacts.

Accordingly, it would be desirable to provide a detector array that collimates and separates the x-ray beams toward individual detector elements to reduce scatter and spectral artifacts. In addition, it is desirable to provide a detector array collimator that protects the gaps between the elements from x-ray beams so that radiation damage, beam hardening, punch through noise and spectral effects of the light reflecting material is minimized.

SUMMARY OF THE INVENTION

These and other objects may be attained by a detector array, which in one embodiment, includes a collimator for reducing scatter, spectral artifacts and x-ray damage. The detector array includes a detector housing, a plurality of detector modules and a collimator having a plurality of collimator plates. Each detector module is mounted to the detector housing and includes a photodiode array optically coupled to a scintillator array. The collimator plates are configured so that x-ray beam signals directed at the scintillator array are allowed to pass and those signals directed toward the gaps in the scintillator array are blocked.

In one embodiment, the detector array is fabricated by spacing and securing each collimator plate to the detector housing so that a x-ray beam shadow is centered over the scintillator gap. More specifically, each collimator plate is positioned so that the centerline of the collimator plate is displaced from, or not collinear with, the centerline of the scintillator array gap. In one embodiment, one wire is then extended the length of the collimator perpendicular to the longitudinal axis of the plates forming a plurality of sections. The number of sections corresponds to the size of the photodiode array so that the X-ray beams are separated to correspond to the number of detector elements.

The above described detector array enables X-ray beams to be separated so that the X-ray beams impinge only on the scintillator array resulting in reduced scatter and spectral artifacts. Additionally, the collimator prevents the x-ray beams from impinging upon the scintillator array gaps. As a result, radiation damage to the scintillator gaps is reduced.

DETAILED DESCRIPTION

Figure 1:
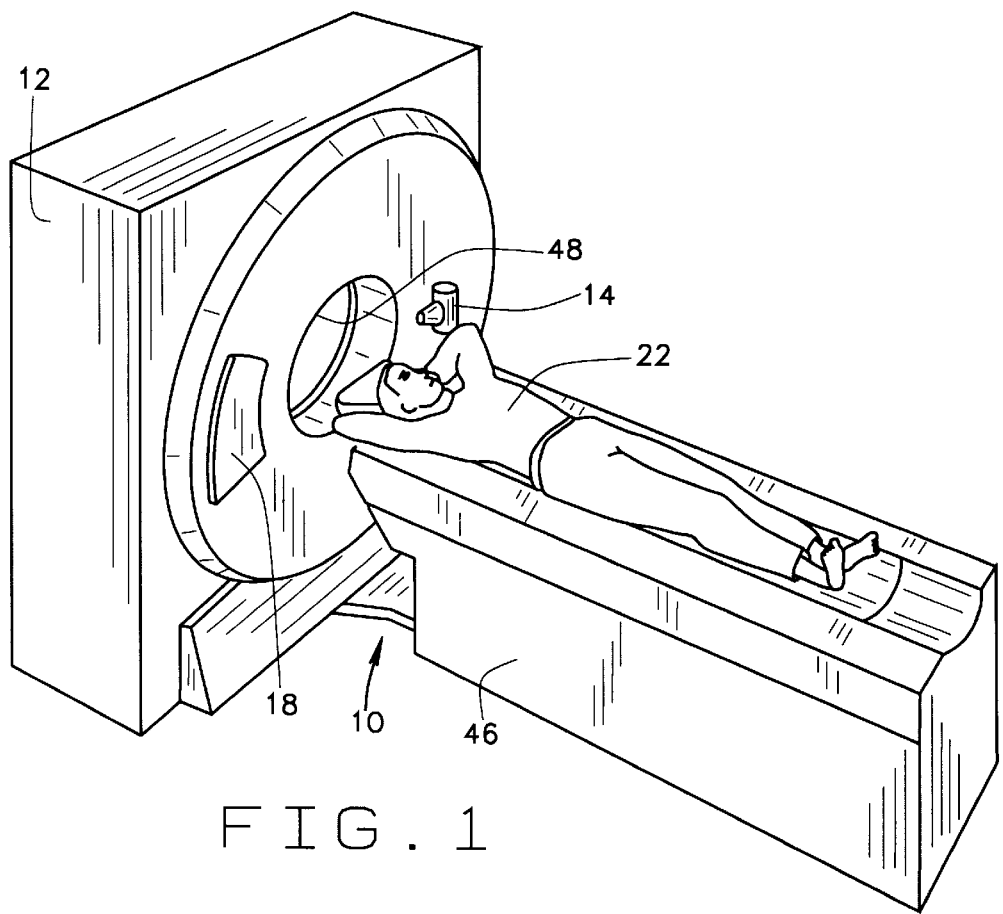
FIG. 1 is a pictorial view of a CT imaging system.
Figure 2:
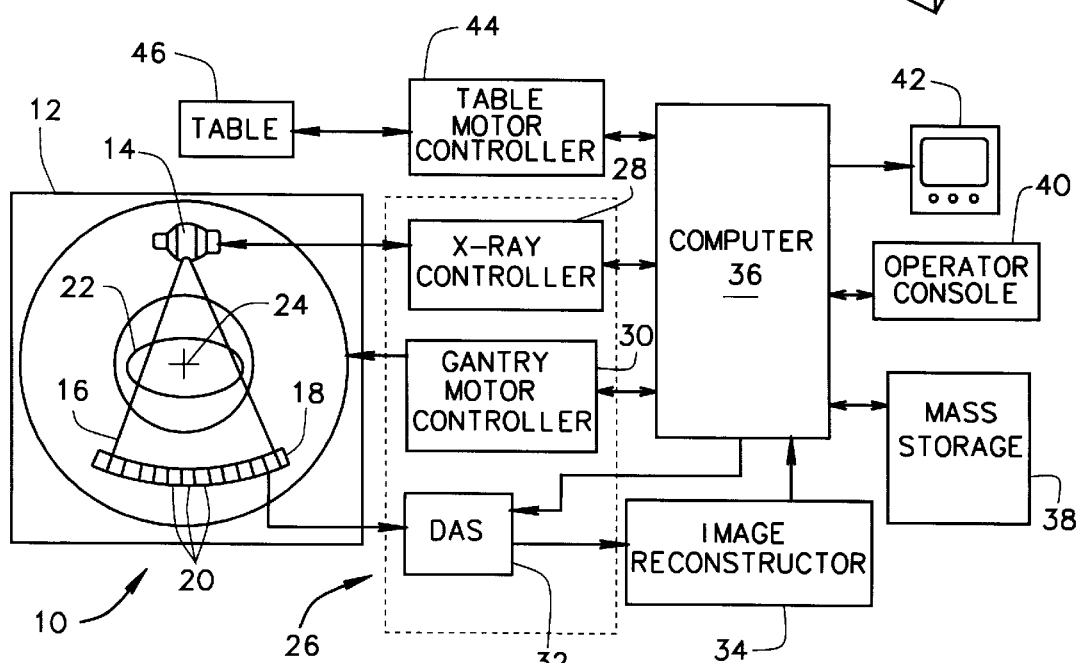
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector modules 20 which together sense the projected x-rays that pass through a medical patient 22. Each detector module 20 produces electrical signals that represent the intensity of impinging x-ray beams and hence the attenuation of the beams as they pass through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector modules 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through a gantry opening 48.

Figures 3, 4:
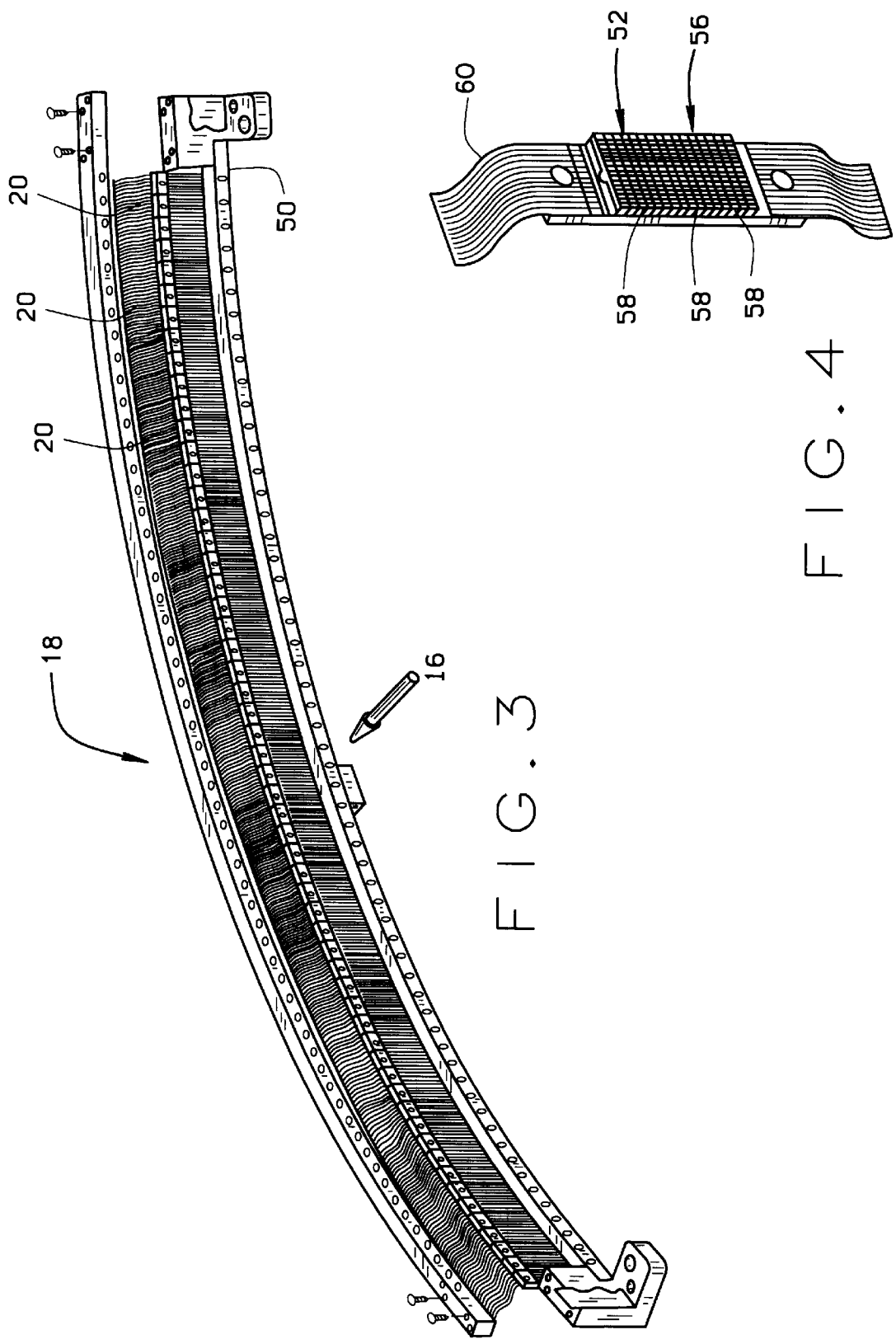
FIG. 3 is a perspective view of a CT system detector array in accordance with the present invention.
FIG. 4 is a perspective view of a detector module shown in FIG. 3.

As shown in FIGS. 3 and 4, detector array 18 includes a plurality of detector modules 20 secured to an arc shaped detector housing 50. Each detector module 20 includes a multidimensional photodiode array 52 and a multidimensional scintillator array 56 positioned in front of and adjacent to photodiode array 52. One photodiode array that may be used is described in copending U.S. patent application Ser. No. 08/978,805, entitled, Photodiode Array For A Scalable Multislice Scanning Computed Tomography System, which is assigned to the present assignee and hereby incorporated herein, in its entirety, by reference. One scintillator array that may be used is described in copending U.S. patent application Ser. No. 08/977,439, entitled, Scintillator For A Multislice Computed Tomograph System, which is assigned to the present assignee and hereby incorporated herein, in its entirety, by reference.

Scintillator array 56 includes a plurality of elements, or cells (not shown) separated by narrow gaps (not shown) between adjacent cells. Scintillator array 56 includes X-axis and Z-axis gaps. The gaps are filled with a light reflective material. Photodiode array 52 includes a plurality of photodiodes 58 which are optically coupled to scintillator array 56. Photodiodes 58 generate electrical output signals 60 representative of the light output by each scintillator of scintillator array 56.

Figure 5:
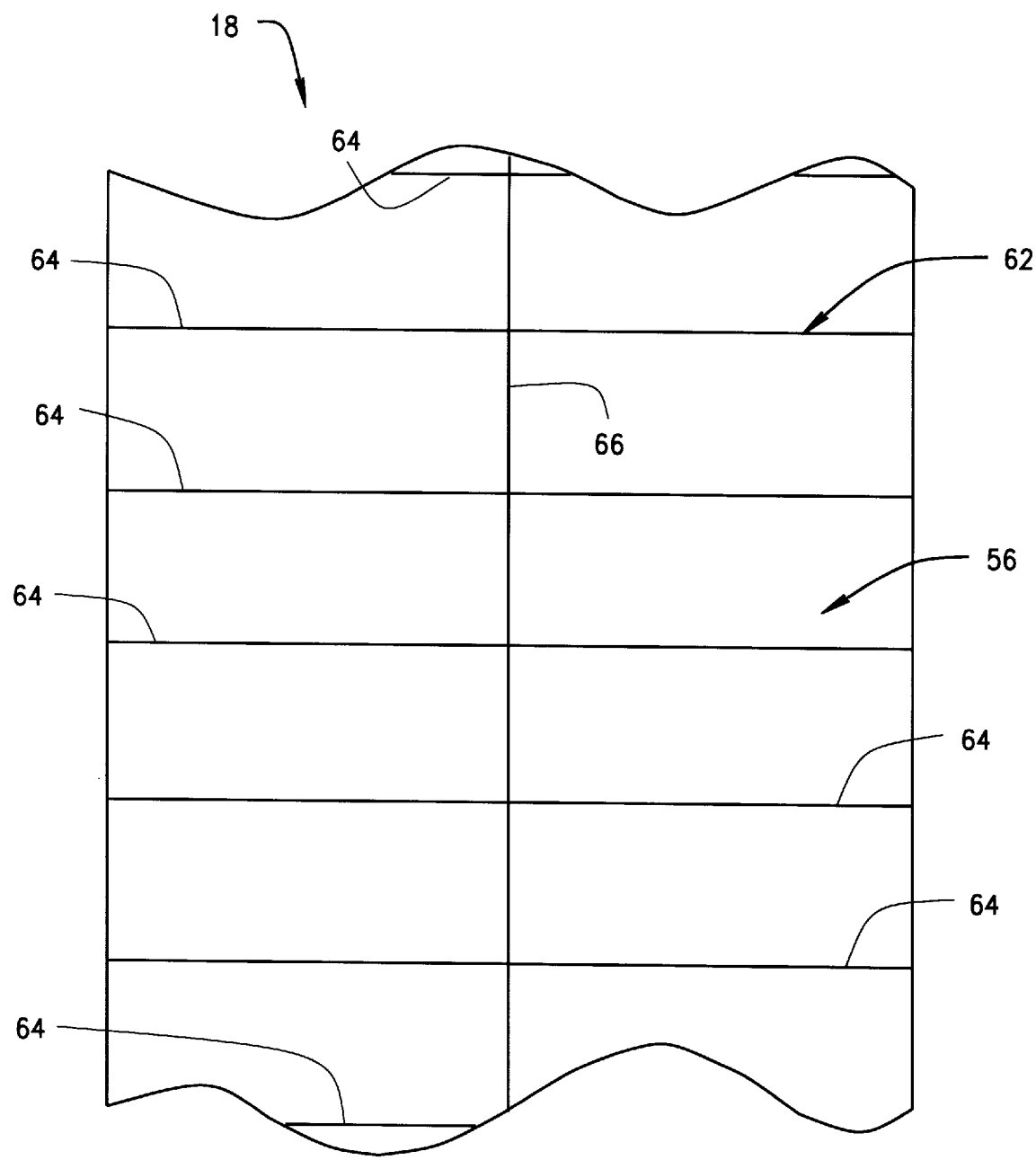
FIG. 5 is a perspective view of a collimator in accordance with the present invention.

Detector array 18 also includes a collimator 62 positioned in front of and adjacent scintillator array 56 to collimate x-ray beams 16 before such beams impinge upon scintillator array 56. Referring to FIG. 5, collimator 62 includes a plurality of plates 64 and at least one wire 66. Plates 64 are spaced and secured together so that the longitudinal axis of each plate 64 extends substantially parallel to the longitudinal axis of each adjacent plate 64. Plates 64 are inserted in slots (not shown) located in housing 50 and bonded at the top and bottom of plates 64. Plates 64 and wire 66 are made, in one embodiment, of tungsten. Wire 66 extends the length of collimator 62 substantially perpendicular to the longitudinal axis of plates 64 and is inserted in horizontal slots (not shown) in plates 64 and bonded.

Figure 6:
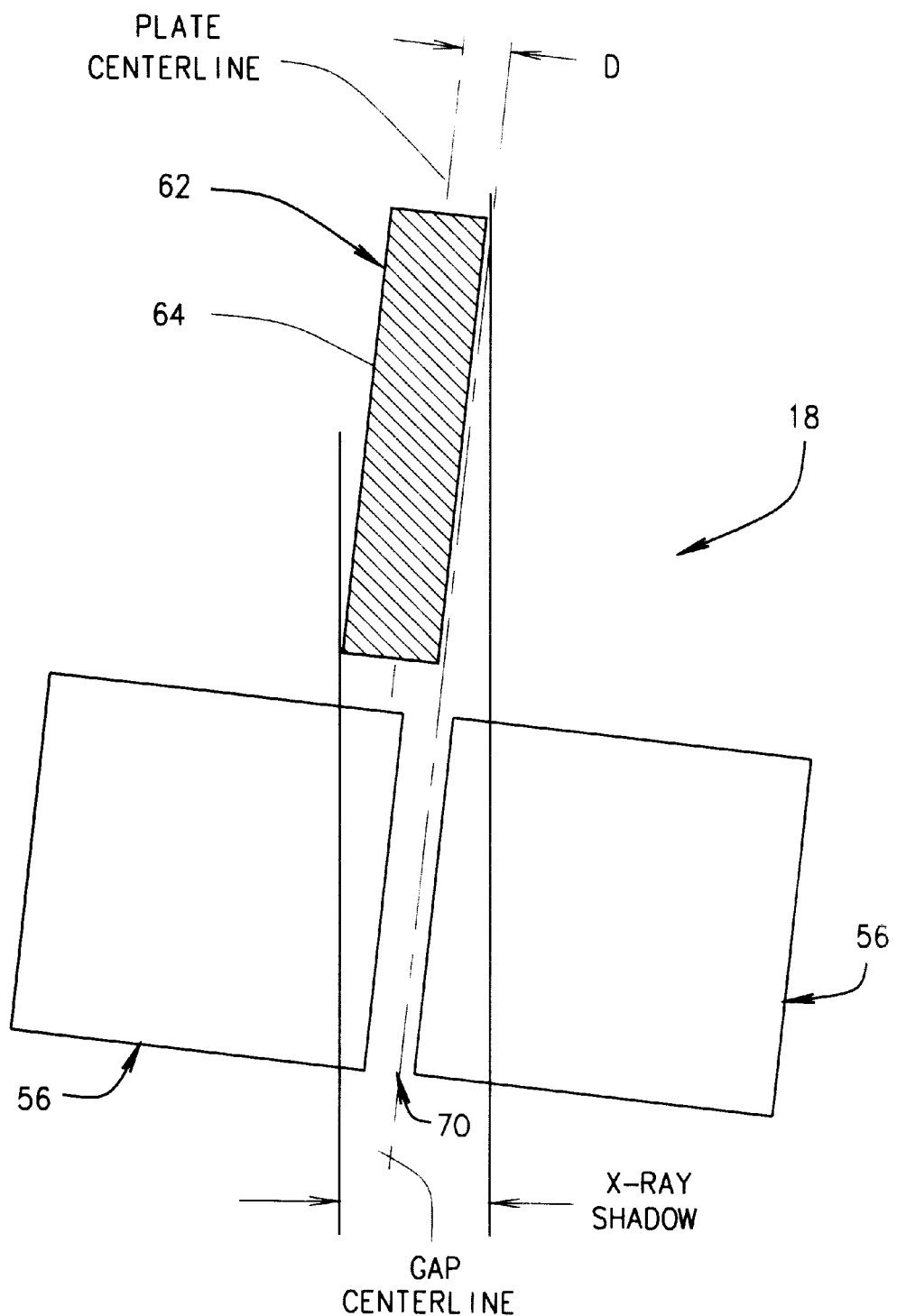
FIG. 6 is a side view of a portion of a detector module shown in FIG. 4.

Referring to FIG. 6, detector array 18 is fabricated by positioning plates 64 over scintillator array X-axis gaps 70 so that the centerline of each collimator plate 64 is displaced from, or not collinear with, the centerline of each scintillator array X-axis gap 70. More specifically and as a result of scintillator array 56 being flat and the radial emission of x-ray beams 16, collimator plates 64 are positioned so that a x-ray shadow is centered over each X-axis scintillator gap 70. In one embodiment, collimator plates 64 are wider than scintillator X-axis gaps 70. For example, X-axis scintillator gaps 70 may be 100 micrometers wide and each collimator plate 64 may be 200 micrometers wide.

In one embodiment, detector modules 20 are secured to detector housing 50 and are skewed, or rotated, along an arc of about ten minutes. Positioning of collimator plates 64 causes the effective collimation aperature for all detector cells (not shown) to increase or decrease signal level similarly as a result of x-axis focal spot motion. Specifically, the signal level of adjacent detector module cells change in a similar direction as a result of x-axis focal spot motion. As a result, differential error caused by x-axis focal spot motion is reduced.

Plates 64 and wire 66 create a plurality of sections (not shown) with each section having an active area and an inactive area (not shown). The active areas separate the X-rays so that x-ray beams 16 are allowed to pass through collimator 62 to scintillator array 56. X-ray beams 16 are prevented from impinging upon scintillator array gaps 70 and from projecting through the edges of scintillator elements by inactive areas created by shadow of collimator 62. More specifically, x-ray beams 16 are prevented from projecting through a shortened path length of scintillator array 52, thereby reducing spectral errors. For example, the centerline of collimator plates 64 may be displaced distance D from the centerline of the gaps 70 so that x-ray beams are prevented from projecting through a portion of scintillator array 56 and so that x-ray beams 16 do not impinge upon the light reflecting material.

The number of sections is dependent on the size of scintillator array 56 and photodiode array 52. The area of scintillator array 56 directly below wire 66 is protected from impinging x-ray beams 16. For example, wire 66 may be positioned above each scintillator array Z-axis gap (not shown) to protect reflective material from radiation damage and reduce penetration of x-ray beams 16 toward photodiode array 52. In one embodiment, the number of collimator wires 66 is one greater than the number of rows in scintillator array 56 so that each gap is protected.

For example, in a sixteen-slice mode of operation, detector array 18 includes fifty-seven detector modules 20. Each detector module 20 includes a photodiode array 52 and scintillator array 56, each having an array size of 16×16 so that array 18 has 16 rows and 912 columns (16×57 modules). As a result, collimator 62 includes seventeen wires 66 and 913 plates 64 allowing sixteen simultaneous slices of data to be collected with each rotation of gantry 12. Additional examples include, a two-slice mode of operation including three wires 66; and a four slice mode of operation including five wires 66. Additional modes beyond those described are possible.

In operation, as x-ray beams 16 are projected toward detector array 18, collimator 62 allows a portion of x-ray beams 16 to impinge upon detector modules 20. Specifically, as x-ray beams 16 are radially emitted from the focal spot of tube 14, a portion of the x-rays impinge scintillator array 56. Those x-ray beams directed to the scintillator gaps are blocked by collimator plates 64 and wires 66. As a result, radiation damage and artifacts are reduced. In addition, centering of the collimator shadow over the scintillator gaps reduces spectral errors caused by movement of the x-ray tube focal spot.

The above described detector array reduces image artifacts by collimating the x-ray beams toward individual detector elements. In addition, the above described detector collimator reduces spectral artifacts by preventing X-ray beams from projecting through the scintillator array elements along a shortened path length. Additionally, the above described detector collimator protects the gaps between the scintillator array elements from x-ray beams so that radiation damage to the light reflecting material is minimized.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A multislice computed tomography system for generating images of an object, said system comprising:

a x-ray source for emitting x-ray beams, said beams emitted from a source focus;

a multislice detector comprising a scintillator array comprising at least first and second cells with a gap therebetween; and a post-patient collimator comprising at least one collimator plate positioned over said scintillator gap so that when x-ray beams are emitted from said x-ray source a shadow of said collimator plate is over said scintillator gap.

2. A system in accordance with claim 1 wherein the centerline of said collimator plate is not collinear with centerline of said scintillator gap.

3. A system in accordance with claim 1 wherein said array comprises at least one X-axis scintillator gap and at least one Z-axis scintillator gap.

4. A system in accordance with claim 3 wherein the centerline of said collimator plate is displaced from the centerline of said X-axis scintillator gap.

5. A system in accordance with claim 3 wherein the width of said collimator plate is greater than the width of said X-axis scintillator gap.

6. A system in accordance with claim 5 wherein said scintillator gap comprises a 100 micrometer gap.

7. A system in accordance with claim 6 wherein said collimator plate is 200 micrometers wide.

8. A system in accordance with claim 3 wherein said scintillator array comprises a plurality of cells.

9. A system in accordance with claim 8 wherein said collimator comprises a plurality of collimator plates.

10. A method of reducing spectral artifacts in a multislice computed tomography system, the system including a x-ray source for emitting x-ray beams, at least one multislice detector comprising a scintillator array having at least first and second cells with a gap therebetween, and a post-patient collimator having at least one collimator plate said method comprising the step of positioning the post-patient collimator plate over the scintillator gap so that when x-ray beams are emitted from the x-ray source a shadow of the collimator plate is over the scintillator gap.

11. A method in accordance with claim 10 wherein positioning the collimator plate over the detector gap comprises the step of positioning the collimator plate so that the collimator plate centerline is not collinear with the scintillator gap centerline.

12. A method in accordance with claim 10 wherein the scintillator array comprises at least one X-axis scintillator gap and at least one Z-axis scintillator gap and wherein positioning the collimator plate over the scintillator gap comprises the step of positioning the collimator plate over the X-axis scintillator gap.

13. A method in accordance with claim 12 wherein said collimator plate comprises a centerline and wherein positioning the collimator plate over the X axis scintillator gap comprises the step of positioning the collimator plate so that the collimator plate centerline is displaced from the X axis scintillator gap centerline.

14. A method in accordance with claim 12 wherein the width of the collimator plate is greater than the width of the X axis scintillator gap.

15. A method in accordance with claim 14 wherein the scintillator gap comprises a 100 micrometer gap.

16. A method in accordance with claim 15 wherein the collimator plate is 200 micrometers wide.

17. A method in accordance with claim 12 wherein the scintillator array includes a plurality of cells and a plurality of collimator plates, and wherein positioning the collimator plate over the X axis scintillator gap comprises the step of positioning the collimator plates over the X axis scintillator gaps.

* * * * *